United States Patent [19]

Young et al.

[11] Patent Number: 4,510,072
[45] Date of Patent: Apr. 9, 1985

[54] COMPOSITION HAVING NEUTRALIZED DIFFERENTIAL INFRARED ABSORBENCY

[75] Inventors: Randall S. Young, Lafayette; Ronald D. Fredericks, Jr., Oakland, both of Calif.

[73] Assignee: Dairy & Food Labs, Inc., San Francisco, Calif.

[21] Appl. No.: 461,720

[22] Filed: Jan. 28, 1983

[51] Int. Cl.³ .............................................. C09K 3/00
[52] U.S. Cl. ................................... 252/380; 250/339; 250/343
[58] Field of Search ............... 252/380; 250/338-345; 356/432, 435, 436, 442

[56] References Cited

U.S. PATENT DOCUMENTS

| | | | |
|---|---|---|---|
| 3,161,768 | 12/1964 | Goulden | 250/43.5 |
| 3,628,916 | 12/1971 | Werner | 23/231 |
| 3,746,511 | 7/1973 | Stookey et al. | 23/231 |
| 3,839,633 | 10/1974 | McKenna et al. | 250/343 |
| 3,876,375 | 4/1975 | Maurukas | 23/230 |
| 3,997,470 | 12/1976 | Monte et al. | 252/408 |
| 4,011,045 | 3/1977 | Bonderman | 23/230 |
| 4,062,800 | 12/1977 | Irick et al. | 252/380 |
| 4,076,983 | 2/1978 | Hopkins et al. | 250/341 |
| 4,125,377 | 11/1978 | Gindler | 23/230 |
| 4,236,075 | 11/1980 | Nexo et al. | 250/343 |
| 4,243,751 | 1/1981 | Swartz | 435/168 |
| 4,247,773 | 1/1981 | Nexo et al. | 250/339 |
| 4,310,763 | 1/1982 | Shields | 250/339 |

OTHER PUBLICATIONS

"The Key to Optimizing Production Profitability" A/S N. Foss Electric Foss America, Inc., reference Milkoscan 104, (4 pp.).
Reference on Milkoscan 203, (8 pp.).

*Primary Examiner*—Ben R. Padgett
*Assistant Examiner*—T. J. Wallen
*Attorney, Agent, or Firm*—Townsend & Townsend

[57] ABSTRACT

A composition which is added to liquid samples undergoing double wavelength infrared analysis exhibits no net differential effect on the double wavelength channels. The composition is formulated by selecting one compensating component for each double wavelength channel, wherein said compensating component offsets the net differential effect exerted by the remainder of the composition.

7 Claims, No Drawings

COMPOSITION HAVING NEUTRALIZED DIFFERENTIAL INFRARED ABSORBENCY

BACKGROUND OF THE INVENTION

The present invention relates generally to compositions which are added to liquid samples being tested for infrared absorbence, and more particularly to a preservative composition which can be added to milk samples and which exhibits a substantially equal increased in infrared absorbence measured at selected pairs of wavelengths.

It is common practice in the dairy industry to send samples of various dairy products to centralized laboratories for testing. Typical measurements include the content of fat, protein, lactose, total solids, and added water. The test samples can be in transit for one or more days between the dairy farm and the central testing laboratory and, even when refrigerated, are subject to bacterial degradation. In order to prevent such degradation (which can affect the composition of the sample as well as foul the test equipment), preservatives are routinely added to the milk sample before leaving the dairy farm.

At the central testing laboratory, the milk sample composition is typically measured based on the infrared absorbence of the sample. The consituents which are to be measured exhibit characteristic absorbencies at different wavelengths, allowing determination of the concentration of each constituent based on the differencce between absorbencies observed at two different wavelengths. In particular, the present invention is concerned with the "double wavelength" determination of milk composition as described in U.S. Pat. Nos. 4,247,773 and 4,236,075 to Nexo et al. That method, which applies broadly to the quantitative measurement of a constituent (dispersed phase) of an emulsion or suspension, relies on the measurement of infrared absorbence at two predetermined wavelengths for each of the constituents to be measured. The first (sample) wavelength is chosen at a frequency where the constituent exhibits a high level of absorbency. The second (reference) wavelength is a frequency where the constituent displays a minimum infrared absorbency. The content of the particular constituent can then be estimated based on the difference between the absorbencies. The wavelength pairs which correspond to the constituent measured will be referred to as "channels" hereinafter.

The accuracy of such a measurement system is limited by cross interference of other components present in the milk. Even in fresh milk, the principle constituents (i.e. fat, protein, and lactose) absorb infrared light at all wavelengths so that the light absorption at any particular wavelength is influenced, to some extent, by all of the constituents present. While this effect can be minimized by selecting wavelengths at which the constituent of interest absorbs strongly and the other constituents absorb less strongly, cross interference cannot be completely eliminated. The analyzer described in U.S Pat. No. 4,236,075, partially compensates for such cross interference by subtracting out the estimated effect of the other constituents based on its initial (uncorrected) measurement. In the example of milk, the lactose absorbency is reduced by the estimated contribution of protein and fat at the lactose wavelength based upon the initial measurements of protein and fat. The measurements of the other constituents are similarly adjusted.

While such iterative adjustment of the measurements works reasonably well to compensate for variations in the concentrations of the principle constituents of an emulsion, it is not able to correct for variations in trace constituents which are not being measured. In particular, the analyzer of U.S. Pat. No. 4,236,075 and similar double wavelength analyzers, are unable to compensate for components which are added to the milk sample, such as the components in a preservative composition. For that reason, the addition of such preservative compositions leads to erroneous measurements. For example, addition of the preservative can affect the measurement of fat, lactose, and protein by as much as 5 to 10% of the actual value.

It would thus be desirable to provide a preservative composition which, when added to fresh milk, will not affect the double wavelength infrared measurement of the milk composition.

SUMMARY OF THE INVENTION

The present invention provides a composition including at least one primary component and one or more compensating component, which composition is formulated to have a neutral effect when added to a liquid sample undergoing double wavelength infrared analysis. The number of primary components is not critical and will depend on the intended use of the composition. The number of compensating components, in contrast, will correspond to the number of constituents (i.e., channels) being measured. Each compensating component is selected to correct the differential effect exerted on a particular pair of wavelengths by the remaining components in the composition. In this way, the absorbency at each of the wavelengths in the pair will be increased by precisely the same amount so that the observed difference in absorbencies will be unaffected by the addition of the composition.

In the usual case, the composition will include a basal formulation having both active and inert primary components. For example, a preservative tablet to be added to milk samples usually contains the active preservative component, an inert vehicle, a dispersing agent, a lubricant, an anti-caking agent, and the like. Each of these components will exhibit infrared absorbence at each of the measured wavelengths, and it will be necessary to assess the net effect of the basal formulation on each of the channels to be measured. The identity and concentrations of each of the compensating components can be determined so that there is no net differential effect on any of the pairs of wavelengths measured.

DESCRIPTION OF THE SPECIFIC EMBODIMENT

The present invention relates to a particular method of infrared analysis known as double wavelength infrared analysis. This method, and an apparatus for performing the method, are described in U.S. Pat. Nos. 4,236,075 and 4,247,773 to Nexo et al., the disclosures of which are incorporated herein by reference. Various components which exhibit infrared absorbence may be measured in a sample, such as milk, by determining the infrared absorbence of the sample at both a sample and a reference wavelength. The sample wavelength is chosen so that the measured component displays a strong absorbency, while the reference wavelength is chosen where the component displays a less strong absorbency. In this way, the difference in absorbencies at the two measured wavelengths will result primarily from the presence of the measured component. This result, of course, is only true if there are no other components in the sample capable of absorbing infrared radiation at the sample and/or reference wavelengths, or such other components which are present absorb equally at both the sample and reference wavelengths.

The composition of the present invention is intended to be added to samples undergoing such double wavelength infrared analysis without adversely affecting the observed differences in absorbence at the particular pairs of reference and sample wavelengths. The invention will be described in reference to a preservative composition which is intended to be added to fresh milk samples which will eventually undergo double wavelength infrared analysis. The invention, however, is not limited to such preservative compositions and instead applies broadly to any compounds or additives which are intended to be introduced into samples undergoing double wavelength infrared analysis.

The present invention contemplates a composition which comprises a basal formulation which includes those compounds which provide the necessary effectivity or reactivity, as well as a number of compensating components which are selected to counteract the infrared absorbency characteristics of the basal formulation at the wavelengths of interest. In the exemplary case of a preservative composition for milk, the basal formulation will include the preservative itself, usually in combination with an inert solid or liquid vehicle. Conveniently, the preservative will be formed into a tablet of an appropriate size for treating the contemplated milk samples and will include anti-caking agents and lubricants which facilitate tablet formation in a machine. Exemplary anti-caking agents include silica, silicon dioxide, and combinations thereof. Suitable lubricants include stearic acid, lauric acid, oleic acid, boric acid, and combinations thereof. The tablet may also include a dispersing agent, such as glucono-δ-lactone, to enhance solution of the tablet in milk.

Compensating components are chosen to offset the observed differential absorbencies at each channel, i.e., measured pair of wavelengths. Thus, when the basal formulation exhibits an absorbency at the sample wavelength which is greater than the absorbency at the reference wavelength, a compensating component must be chosen which will have the opposite effect, i.e., exhibit a greater absorbency at the reference wavelength than at the sample wavelength. By incorporation the proper amount of the compensating component, the total absorbency added to the sample by the subject composition at each of the two wavelengths will be substantially equal. Of course, when calculating the required amount of each compensating component, the net effect of all other components, including both primary and compensating components, must be taken into account. This can be achieved by adding the absorbence of each of the compensating components (at each wavelength of interest) to the measured absorbence of the basal formulation. The required amounts of each compensating component are those amounts which cause a zero differential effect on each measured channel. The amounts can be estimated on linear regression analysis based on the known infrared absorbence characteristics of each compensating component. Usually, the formulation will be further adjusted until the observed differential effects are eliminated.

A wide variety of substances are suitable for use a compensating components. Conveniently, the compensating components will be soluble in the sample medium, display uniform infrared absorbency characteristics regardless of source, and be inexpensive. For aqueous solutions, alkali metal salts, alkaline earth salts, organic acids, and the like will be suitable. As a final consideration, the compensating components must be chosen to be inert in the sense that they will not react with the basal formulation or the sample, or otherwise interfere with the intended use of the composition. For the exemplary case of milk, suitable compensating components include pthalimide, sodium acetate, sodium tartrate, citric acid, lactose monohydrate, ascorbic acid, and the like. Also, sometimes it will be possible to adjust the amount of one of the primary components so that said primary component replaces one of the compensating components. Of course, the amount of such a primary component cannot be critical to the basal formulation since the amount will depend on the need to balance absorbencies.

It will be necessary to add one compensating component for each channel or pair of wavelengths which are being measured. Once a basal formulation has been selected, the effect on the infrared absorbency of the sample must be determined. This is most conveniently accomplished by adding the basal formulation to the sample and measuring the absorbencies at both wavelengths in each wavelength pair of interest. In this way, the differential effect at each wavelength pair can be used to select the appropriate compensating component. In the exemplary case, a basal preservative composition will be added to the sample of milk and infrared absorbencies measured at selected pairs of wavelengths, as follows:

| CHANNEL | | WAVELENGTH (μ) |
|---|---|---|
| Fat a | Sample | 5.7 |
| | Reference | 5.5 |
| Fat b | Sample | 3.4 |
| | Reference | 3.5 |
| Protein | Sample | 6.5 |
| | Reference | 6.7 |
| Lactose | Sample | 9.65 |
| | Reference | 7.82 |

By comparing the absorbence of the fresh milk sample with that of the milk-preservative sample, the differential absorbency is calculated.

In general, the absorbence observed at the sample and reference wavelengths will not be the same for any of the channels measured. Even if they are the same for one or more channels, a compensating component will still have to be included to offset the effects on the channel brought about by the addition of the other compensating components. In any event, a compensating component is selected for each channel so that said compensating component counteracts the observed effect of the basal formulation. That is, if the particular channel displays a greater absorbence at the sample wavelength than at the reference wavelength, the compensating component should be selected to exhibit a greater absorbence at the reference wavelength. Such a selection is repeated for each of the channels and, by knowing the absorbency coefficients of each of the compensating components, the approximate amount of each compensating required to offset the basal formulation can be calculated.

Instead of measuring the actual absorbence at both wavelengths in each wavelength pair, the double wavelength infrared analyzer can be used to determine the overall formulation. The basal formulation is added to a milk sample, and a routine milk analysis performed. By comparing the results of the fat, protein and lactose measurements with those measurements on a fresh milk sample, the net differential effect of the basal formulation is apparent. Moreover, the net differential effect of a number of compensating compounds can also be determined by adding them alone to milk samples and comparing the observed measurement to the same measurements for untreated samples. In this way, a table of compensating compounds having both positive and negative net effects of a varying degrees can be generated. These compensating compounds can be selected individually to offset the observed effects on each measurement channel. Again, it will be necessary to take into account the effect of each of the compensating components, as well as the effect of the basal formulation, at each measuring channel. This, however, can be easily handled by well known linear regression techniques.

In formulating the compositions of the present invention, certain common sense rules should be applied. When choosing a compensating component, it is desirable that it exhibit a strong differential absorbence at the channel of interest and minimal differential absorbencies at all other or most other channels. In this way, the amount of the compensating component which must be added is minimized and the effect on the other channels is reduced. Also, because of the effect of the other compensating components, the calculated amount of a compensating component to be added will sometimes be a negative value. This means that the other compensating components have more than offset the differential absorbence exerted on the channel by the basal formulation. Another compensating component having the opposite differential effect on the channel should be chosen and substituted for the one which led to a negative value. The required amounts of each compensating component can then be recalculated. Finally, the total amount of compensating components added must fall within parameters consistent with the desired dosage or tablet size. By utilizing components with strong absorbencies at the particular channels, however, this final objective should be met.

The following examples are offered by way of example and not by way of limitation.

EXPERIMENTAL

1. Measurement of Net Differential Effect Caused by Addition of Particular Components The shifts in fat, protein and lactose measurements caused by the addition of certain compounds were measured, and the results are listed in Table 1. The measurements were performed by adding known amounts of each compound to 50 g fresh whole milk samples, measuring the fat a, fat b, protein, and lactose content in a double wavelength infrared analyzer, and comparing the observed results with those for samples of the same milk without the compounds added. The results are reported as the difference determined by subtracting the measurement of the sample with the compound added from the measurement of the sample without the compound. Thus, the negative value indicates that the compound is more absorbent at the reference wavelength than at the sample wavelength, while a positive value indicates the opposite.

Measurements of fat a, protein and lactose were performed in a Milko-Scan Model 203a analyzer. Measurements of fat b, protein and lactose were made in a Milko-Scan Model 203b analyzer. For each compound, twenty replications with the compound added and twenty replications without the compound added were run in each analyzer. Thus, the values in Table 1 are the average of forty replications for both protein and lactose, and twenty replications for both fat b and fat a.

TABLE 1

| Compound[1] | Fat b | Fat a | Protein | Lactose |
|---|---|---|---|---|
| KCL | (0.170)[10] | (0.100) | (0.050) | 0.000 |
| NaCl[2] | (0.190) | (0.100) | (0.020) | 0.040 |
| NaCl[3] | (0.199) | (0.067) | (0.063) | (0.009) |
| Bronopol[4] | 0.025 | (0.055) | 0.215 | 0.223 |
| Boric Acid[5] | 0.240 | 0.070 | (0.760) | 0.300 |
| Boric Acid[6] | 0.050 | 0.094 | (0.549) | 0.436 |
| Cyloid[6] | (1.000) | 1.000 | (1.250) | 0.250 |
| SiO$_2$ | 0.000 | 0.000 | 0.500 | 1.250 |
| Stearic Acid[6] | 3.500 | 0.500 | 2.000 | 1.750 |
| Stearic Acid[7] | 0.000 | 0.050 | 0.000 | 0.000 |
| Glucono-δ-lactone[8] | 0.169 | 0.080 | (0.110) | (0.070) |
| Glucono-δ-lactone[9] | 0.318 | 0.218 | 0.209 | 0.299 |
| Pthalimide | (0.025) | 1.741 | 0.162 | 0.299 |
| Sodium Acetate | 0.250 | (0.170) | 2.480 | 0.000 |
| Sodium Tartrate | 0.190 | (0.050) | 0.430 | 0.050 |
| Citric Acid | 0.561 | 0.180 | 0.371 | (1.152) |
| Lactose Monohydrate | 0.000 | 0.016 | 0.028 | 0.956 |
| Ascorbic Acid | 0.140 | 0.340 | 0.510 | 0.000 |
| Milk | 0.000 | 0.000 | 0.000 | 0.000 |

[1] 1% addition to 50 g sample of fresh whole milk.
[2] Star Flake dendritic salt from Morton Salt Co.
[3] ES dendritic salt from Morton Salt Co.
[4] Boots Chemical Co., Ltd., London, United Kingdom
[5] Alchemist, Dublin, CA
[6] Winning, Cost Mesa, CA
[7] Flake (Grade II) 90%, Sigma Chemical Co., St. Louis, MO
[8] Pfizer, New York, NY (medical grade)
[9] Pfizer (veterinary grade)
[10] Values in parentheses are negative.

2. Preparation of Preservative Composition without Compensating Compounds

A preservative composition including a biocide (Bronopol ®), a vehicle (sodium chloride), a dispersing agent (glucono-δ-lactone) and lubricants (boric acid and stearic acid) was prepared as set forth in Table 2. Such a formulation is suitable for making tablets. The predicted total effect on each of the fat a, fat b, protein and lactose channels was based on the calculated effect of each component on each channel, which in turn was obtained by multiplying weight percent of the component by the appropriate coefficient in Table 1.

TABLE 2

| Component | Wt. (mg) | Wt. % | Fat b Coeff. | Fat b Eff. | Fat a Coeff. | Fat a Eff. | Protein Coeff. | Protein Eff. | Lactose Coeff. | Lactose Eff. |
|---|---|---|---|---|---|---|---|---|---|---|
| Bronopol ® | 12.00 | 0.0240 | 0.0025 | 0.006 | (0.055)[1] | (0.0013) | 0.215 | 0.0052 | 0.223 | 0.0054 |
| Sodium Chloride | 54.00 | 0.1080 | (0.190) | (0.0205) | (0.100) | (0.0108) | (0.020) | (0.0022) | 0.040 | 0.0043 |
| Glucono-δ-lactone | 20.88 | 0.0418 | 0.169 | 0.0071 | 0.080 | 0.0033 | (0.110) | (0.0046) | (0.070) | (0.0029) |
| Boric Acid | 1.20 | 0.0024 | 0.240 | 0.0006 | 0.070 | 0.0002 | (0.760) | (0.0018) | 0.300 | 0.0007 |
| Stearic Acid | 0.60 | 0.0012 | 0.000 | 0.0000 | 0.050 | 0.0006 | 0.000 | 0.0000 | 0.000 | 0.0000 |
| Calculated Total Effect | | | | (0.0122) | | (0.0080) | | (0.0034) | | 0.0075 |

TABLE 2-continued

| Component | Wt. (mg) | Wt. % | Fat b Coeff. | Eff. | Fat a Coeff. | Eff. | Protein Coeff. | Eff. | Lactose Coeff. | Eff. |
|---|---|---|---|---|---|---|---|---|---|---|
| Measured Total Effect | | | | (0.0037) | | (0.0145) | | (0.0045) | | 0.0010 |

[1] Values in parentheses are negative.

The actual effect of the tablet on each measurement channel was then determined on the Milko-Scan Model 203a and 203b analyzers. Twenty samples with the tablet and twenty samples without the tablet were run on each analyzer and the results shown on Table 2 are the averages. While the predicted and actual values do not agree precisely, the predicted values are useful in choosing an initial formulation that will not have an unreasonable effect on any one channel.

3. Selection of Compensating Compounds and Calculation of Required Amounts

Observing the Measured Total Effect (MTE) at each channel on Table 2, suitable compensating compounds can be selected from Table 1. For example, since the MTE on the fat b channel is negative, a compensating compound having a positive effect on the fat b channel is required. For this example, glucono-δ-lactone is selected. Similarly, a compensating compound having a positive effect on the fat a channel is required to offset the observed negative effect of the basal formulation. Pthalimide is the best choice since it exhibits a very high positive effect on the fat b channel, with much smaller effects on the other channels. Sodium acetate is selected to correct the negative effect on the protein channel, while citric acid is selected to correct the positive effect on the lactose channel.

The required amounts of each of the compensating components are determined so that the total composition displays approximately a zero net effect on each channel. These amounts are set forth in Table 3.

| Component | Wt. (mg) |
|---|---|
| Boric acid | 1.25 |
| Stearic acid | 0.52 |
| SiO$_2$ | 1.15 |
| Glucono-δ-lactone | 49.69 |
| Pthalimide | 0.42 |
| Sodium acetate | 1.35 |
| Citric acid | 1.04 |

The measured effect of this tablet on a 50 ml sample of fresh milk is as follows:

| | Fat b | Fat a | Protein | Lactose |
|---|---|---|---|---|
| Absolute | 0.0020% | 0.0005% | 0.0005% | (0.0023%) |

These figures are the absolute effect on the percentage indicated by the infrared analyzer. Thus, the fat b measurement, which is typically about 4%, will be increased by a relative percentage of about 0.05. This is in contrast to the formulations of the prior art which typically introduced an error as great as ±10%. Similar improvement is displayed on all channels.

Although the foregoing invention has been described in detail by way of illustration and example for purposes of clarity of understanding, it will be obvious that certain changes and modifications may be practiced within the scope of the appended claims.

In particular, the form of the composition is not lim-

TABLE 3

| Compensating Component | Wt. (mg) | Wt. %[1] | Fat b Coeff.[2] | Eff.[3] | Fat a Coeff. | Eff. | Protein Coeff. | Eff. | Lactose Coeff. | Eff. |
|---|---|---|---|---|---|---|---|---|---|---|
| Glucono-δ-lactone[4] | 7.10 | 0.0142 | 0.169 | 0.0024 | 0.080 | 0.0011 | (0.110)[5] | (0.0016) | (0.070) | (0.0010) |
| Pthalimide | 3.80 | 0.0076 | (0.025) | (0.0002) | 1.741 | 0.132 | 0.162 | 0.0012 | 0.299 | 0.0023 |
| Sodium acetate | 0.80 | 0.0016 | 0.250 | 0.0004 | (0.170) | 0.0003 | 2.480 | 0.0040 | 0.000 | 0.0000 |
| Citric acid | 1.00 | 0.0020 | 0.561 | 0.0011 | 0.180 | 0.0004 | 0.371 | 0.0007 | (1.152) | (0.0023) |
| TOTAL EFFECT OF COMP. COMPONENTS | | | | 0.0037 | | 0.0144 | | 0.0043 | | (0.0010) |
| NET EFFECT OF BASAL FORMULATION[6] | | | | (0.0037) | | (0.0145) | | (0.0045) | | 0.0010 |
| OVERALL EFFECT OF COMPOSITION | | | | 0.000 | | (0.0001) | | (0.0002) | | 0.0000 |

[1] Based on total weight of 101.68 mg.
[2] From Table 1
[3] Wt. % × Coeff.
[4] Pfizer, New York, NY (medical grade)
[5] Values in parentheses are negative.
[6] From Table 2.

4. Adjustment of Formulation

The blend calculated in Table 3 was prepared and tested. The powder was overly hydroscopic causing the tableting press to jam due to excessive moisture buildup. Also, the resulting tablets were brittle and tended to break apart. Finally, the tablet composition continued to display an effect (although greatly reduced) on the measurements of fat, protein and lactose.

A revised formulation was prepared as follows:

| Component | Wt. (mg) |
|---|---|
| Sodium chloride | 13.13 |
| KCl | 43.02 |
| Bronopol ® | 12.50 |
| Sodium bromcresol purple | 0.94 | ited to tablets and includes liquids, powders aerosols, dusts, and the like. Moreover, the use of the composition is not limited to the treatment of liquid samples. Instead, the composition can be used to treat any form of sample amenable to infrared absorbence analysis, including powders, flakes, fabrics, pellets, and the like.

What is claimed is:

1. A composition which, when added to a liquid sample, will exhibit an equivalent increase in infrared absorbence at preselected first and second wavelengths, said composition comprising:
   one or more primary components which together exhibit a first absorbency at said first wavelength and a second absorbency at said second wavlength; and a compensating component which exhibits a first absorbency at said first wavelength and a second absorbency at said second wavelength, said compensating component being present in a predetermined amount so that the sum of the first absorbencies of both the primary and compensating components will substantially equal the sum of the second absorbencies of both the primary and compensating components.

2. A composition which, when added to a liquid sample, will increase the infrared absorbence of the sample by a substantially equal amount at both wavelengths in a plurality of preselected pairs of wavelengths, said composition comprising:

one or more components which together exhibit an absorbency which differs the two wavelengths in each pair of wavelengths; and a plurality of compensating components equal in number to the preselected pairs and which exhibit preselected absorbency characteristics, each of said compensating components being present in predetermined amounts so that the collective absorbency of the composition is the same at both wavelengths in each pair of wavelengths.

3. A composition including a plurality of components wherein the infrared absorbence characteristics and relative amounts of at least some of the components are selected so that, when added to a liquid sample, the composition increases the infrared absorbence of the liquid by a substantially equal amount at both wavelengths in a plurality of presented pairs of wavelengths.

4. A composition as in claim 3, wherein one of the components is a biocide.

5. A composition as in claim 3, wherein the pairs of wavelengths are selected to allow measurement of the content of fat, protein and lactose in milk.

6. A preservative composition for adding to milk samples which will be subjected to infrared absorbence testing, said testing comprising:

measuring the relative absorbence of the sample at a first pair of wavelengths to determine fat content;

measuring the relative absorbence of the sample at a second pair of wavelengths to determine protein content; and measuring the relative absorbence of the sample of a third pair of wavelengths to determine lactose content;

said composition comprising:

one or more components, including a biocide, which together exhibit differing absorbencies at each wavelength in the three pairs of wavelengths;

a first compensating component having absorbency characteristics and present in an amount so that the total increase in absorbency observed at both wavelengths of the first pair of wavelengths is substantially equal;

a second compensating component having absorbency characteristics and present in an amount so that the total increase in absorbency observed at both wavelengths of the second pair of wavelengths is substantially equal; and a third compensating component having absorbency characteristics are present in an amount so that the total increase in absorbency observed at both wavelengths of the third pair of wavelengths is substantially equal.

7. A preservative composition as in claim 6, wherein the relative absorbence of the milk samples is measured at at least one additional pair of wavelengths and the composition includes one additional compensating component for each additional pair of wavelengths.

* * * * *